United States Patent
Afriat et al.

(10) Patent No.: US 6,331,306 B1
(45) Date of Patent: *Dec. 18, 2001

(54) COMPOSITION IN THE FORM OF A WATER-IN-OIL EMULSION HAVING A CHANGING SHEAR RATE

(75) Inventors: Isabelle Afriat, Paris; Virginie Boulier, Paray-Vieille-Poste, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/343,527

(22) Filed: Jun. 30, 1999

(30) Foreign Application Priority Data

Jul. 1, 1998 (FR) .................................. 98 08418

(51) Int. Cl.$^7$ ........................................ A61K 7/48
(52) U.S. Cl. .................. 424/401; 424/78.03; 424/617; 514/844; 514/863; 514/937; 514/938; 514/944
(58) Field of Search ................. 424/401, 78.03, 424/617; 514/844, 863, 944, 937, 938

(56) References Cited

FOREIGN PATENT DOCUMENTS 2 242 358 * 2/1991 (GB).

* cited by examiner

Primary Examiner—S. Mark Clardy
Assistant Examiner—Michael A. Williamson
(74) Attorney, Agent, or Firm—Oblon, Spivak, McClelland, Maier & Neustadt, P.C.

(57) ABSTRACT

A cosmetic or dermatological composition, comprising:

an aqueous phase dispersed in an oily phase with a silicone emulsifying agent, wherein the viscosity of the composition, measured with a Rheomat 180 viscometer at a shear rate of 200 s$^{-1}$ and at 25° C., ranges from 3 Pa.s (30 poises) to 20 Pa.s (200 poises), the aqueous phase constituting at least 78% by weight with respect to the total weight of the composition with the water of the aqueous phase constituting at least 65% of the total weight of the composition, and the emulsifying agent consisting of the dimethicone copolyol of formula (I):

wherein R$^1$ is

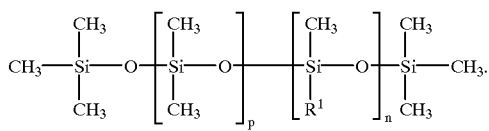

16 Claims, No Drawings

COMPOSITION IN THE FORM OF A WATER-IN-OIL EMULSION HAVING A CHANGING SHEAR RATE

BACKGROUND OF THE INVENTION

1. Field of the Invention

The present invention relates to a composition which is in the form of a water-in-oil (W/O) emulsion, which has a viscosity, at a shear rate of 200 s−1 and at 25° C., ranging from 3 Pa.s (30 poises) to 20 Pa.s (200 poises) and which comprises a specific silicone surfactant and has a high water content. The present composition has the appearance of a cream and can be used in particular in the cosmetic and/or dermatological fields.

2. Background of the Invention

In the cosmetic or dermatological fields, it is commonplace to use compositions having the appearance of a cream and which are composed of a water-in-oil (W/O) emulsion comprising an aqueous phase dispersed in an oily phase. These emulsions comprise a continuous oily phase and, therefore, make it possible to form, at the surface of the skin, a lipid film which prevents transepidermal water loss and protects the skin from outside attacks. These emulsions are particularly appropriate for protecting and nourishing the skin and in particular for treating dry skin.

A cream is, in the fields under consideration, a composition exhibiting a degree of viscosity, in contrast to liquid or semi-liquid compositions, such as lotions and milks, or to solid compositions. However, creams in the form of W/O emulsions exhibit the disadvantage of contributing a fairly greasy feel to the skin on application, the oily phase being the external phase. Thus, these creams are generally used for dry skin, since they are too greasy to be used on greasy skin. Furthermore, W/O emulsions do not contribute any freshness and are generally too rich in oils to be used during the summer or in hot countries.

To overcome these disadvantages, the preparation of emulsions with a high water content has been proposed. However, the water content of the compositions cannot be too high for reasons of stability, otherwise a high water content has to be compensated for by the addition of several surfactants or of gelling agents, which can be harmful to the comfort of the final composition and can even lead to problems of cutaneous irritation, in particular, in people with sensitive skin.

A need, therefore, remains for a composition which has the viscosity of a cream and which is provided in the form of a stable water-in-oil emulsion, which comprises a large amount of water and which can be used in the cosmetic and/or dermatological fields, which does not exhibit the disadvantages of the prior art.

SUMMARY OF THE INVENTION

Accordingly, one object of the present invention is to provide a cosmetic or dermatological composition for the protection of the skin which, as an emulsion, does not impart a greasy feeling to the skin.

Briefly, this object and other objects of the present invention as hereinafter will become more readily apparent can be attained by a composition comprises an aqueous phase dispersed in an oily phase containing a silicone emulsifying agent, which composition has a viscosity, measured with a Rheomat 180 viscometer at a shear rate of 200 s$^{-1}$ and at 25° C., ranging from 3 Pa.s (30 poises) to 20 Pa.s (200 poises), said composition comprising at least 78% by weight of aqueous phase, with respect to the total weight of the composition, including at least 65% of water with respect to the total weight of the composition, and in that the composition comprises, as sole emulsifying agent, the dimethicone copolyol of formula

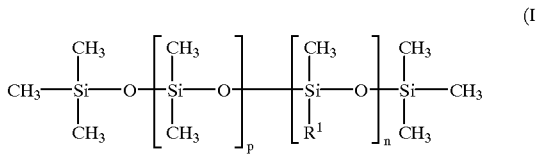

in which $R^1$ represents

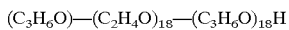

p=394 and n=4.

DETAILED DESCRIPTION OF THE PREFERRED EMBODIMENTS

In spite of the presence of a large amount of water in the present composition, the composition of the invention is stable over time. In addition, it has a specific rheological characteristic which renders it useful in the fields under consideration particularly advantageous. This is because, during the application to the skin, the composition "breaks", that is to say that it suddenly fluidizes under the effect of shearing, which is probably attributable to the phenomenon of rupturing within the emulsion. Thus, the composition of the invention contributes very great freshness to the skin.

The composition of the invention has a viscosity ranging from 3 Pa.s (30 poises) to 20 Pa.s (200 poises). This viscosity is measured with a Rheomat 180, that is to say with the RM 180 Rheomat device manufactured by Mettler.

The composition of the invention comprises at least 78% by weight of aqueous phase with respect to the total weight of the composition and preferably at least 80% of the total weight of the composition. The aqueous phase can constitute up to 92% of the total weight of the composition.

Water constitutes at least 65% and preferably at least 70% of the total weight of the composition.

Furthermore, the aqueous phase of the emulsion can comprise at least one lower molecular weight alcohol such as ethanol, in an amount preferably ranging up to 15%, preferably up to 10% of the total weight of the composition and one or more polyols such as glycerol or propylene glycol in an amount ranging, for example, up to 20%, preferably up to 10% of the total weight of the composition.

Furthermore, the composition of the invention comprises, as sole emulsifying agent, the dimethicone copolyol of formula (I). This dimethicone copolyol can be provided in the form of a mixture with a volatile or non-volatile silicone oil and in particular with cyclomethicones (D4 or D5) and/or polydimethylsiloxanes of different viscosities, in particular 5 cSt and 10 cSt. Suitable such mixtures are commercially available, for instance, those as follows sold by the Dow Corning Company:

(i) a mixture of compound of formula (I), of tetracyclomethicone (D4) and of water (ratio by weight 10/88/2), sold under the name DC 3225C;

(ii) a mixture of compound of formula (I), of pentacyclomethicone (D5) and of water (ratio by weight 10/88/2), sold under the name DC 5225C, (iii) a mixture of compound of formula (I) and of polydimethylsiloxane 5 cSt (ratio by weight 10/90), sold under the name DC 3225C in 200 Fluid 5 cSt;

(iv) a mixture of compound of formula (I) and of polydimethylsiloxane 10 cSt (ratio by weight 10/90), sold under the name DC 3225C in 200 Fluid 10 cSt;

(v) a mixture of compound of formula (I) and of pentacyclomethicone (D5) (ratio by weight 43/57), sold under the name DC 5185C.

The emulsifying agent of the formula (I) is preferably present in an amount of active material ranging from 0.5–5%, preferably from 0.6–2% by weight with respect to the total weight of the composition.

Although the composition is devoid of any other emulsifying agent, the composition obtained is stable over time.

The ratio by weight of oily phase to emulsifying agent is preferably equal to or greater than 5, preferably equal to or greater than 8.

The oily phase of the composition of the invention can comprise, in addition to the silicone oil, optionally, as a mixture with the emulsifying agent, any kind of oil and fatty substance well-known to one of skill in the art such as oils of vegetable origin, oils of animal origin, synthetic oils and in particular fatty esters, silicone oils, fluorinated oils and/or mineral oils, as well as mixtures of these oils.

The oily phase of the composition of the invention preferably comprises at least one volatile silicone oil generally present in an amount ranging from 6–16% by weight with respect to the total weight of the emulsion, such as, for example, a cyclic silicone, such as pentacyclomethicone, tetracyclomethicone or hexacyclomethicone.

The oily phase can additionally comprise other fatty constituents such as fatty alcohols and fatty acids.

The oily phase is present in the composition of the invention in an amount ranging from 8–22%, preferably from 12–20% by weight with respect to the total weight of the composition.

Another advantage of the composition of the invention arises from the fact that a large amount of electrolyte can be incorporated therein without harming the stability of the composition. Suitable such electrolytes include salts of mono-, di- or trivalent metals and more particularly alkaline earth metal salts such as barium, calcium and strontium salts; alkali metal salts such as sodium and potassium salts, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon and selenium salts, and their mixtures.

The ions constituting these salts can be selected, for example, from carbonates, bicarbonates, sulfates, glycerophosphates, borates, chlorides, bromides, nitrates, acetates, hydroxides, persulfates and salts of α-hydroxy acids such as citrates, tartrates, lactates and malates and of fruit acids, or alternatively salts of amino acids such as aspartate, arginate, glycocholate and fumarate.

The electrolyte is preferably a mixture of salts comprising in particular calcium, magnesium and sodium salts and in particular a mixture comprising at least magnesium chloride, potassium chloride, sodium chloride, calcium chloride and magnesium bromide, the said mixture corresponding to Dead Sea salts.

The content of electrolyte, when it is present, generally ranges from 0.5–20%, preferably from 2.5–10% by weight with respect to the total weight of the composition.

The composition of the invention is preferably intended for topical care or treatment. In this case, the emulsion must comprise a physiologically acceptable medium, that is to say compatible with the skin, mucous membranes, nails, scalp and/or hair. In addition, it preferably comprises at least one active principle and is applied in a large number of cosmetic and/or dematological treatments of the skin, including the scalp, hair, nails and/or mucous membranes, in particular for the care of and/or the making-up of and/or the anti-sun protection of the skin and/or mucous membranes, as well as for the preparation of a cream intended for the treatment of diseases of the skin, more particularly of greasy skin (contribution of freshness) and of psoriasis, as product for accompanying the treatment.

Another aspect of the invention is, therefore, a topical composition comprising an emulsion as defined above and at least one active principle.

Other active ingredients which may be included in the composition include, in addition to the electrolytes indicated above, of polyols such as glycerol, glycols such as polyethylene glycol 8, and sugar derivatives, enzymes, natural extracts, procyanidol oligomers, vitamins such as vitamin C, vitamin E, vitamin A and their esters, phosphate and glucosyl derivatives, urea, rutin, depigmenting agents such as kojic acid and caffeic acid, β-hydroxy acids such as salicylic acid and its derivatives, α-hydroxy acids such as lactic acid and glycolic acid, retinoic acid and its derivatives, screening agents, moisturizing agents, such as protein hydrolysates, and their mixtures.

These active ingredient can be present, for example, in a concentration ranging from 0.01–20%, preferably from 0.1–5% and more preferably from 0.5–3% of the total weight of the composition.

In a known way, the composition of the invention can also comprise adjuvants which are normally used in the cosmetic and/or dermatological fields, such as preservatives, antioxidants, complexing agents, solvents, fragrances, fillers, screening agents, bactericides, odor absorbers, coloring materials and lipid vesicles. The amounts of these various adjuvants are those conventionally used in the field under consideration, for example from 0.01–20% of the total weight of the composition. These adjuvants, depending on their nature, can be introduced into the fatty phase, into the aqueous phase and/or into the lipid vesicles.

A further aspect of the present invention is a process for the cosmetic treatment of the skin, hair, nails, scalp and/or mucous membranes utilizing the composition as described above.

Another aspect of the invention is the use of the composition as defined above for the manufacture of a cream intended for the treatment of greasy skin.

When the present composition comprises Dead Sea salts, the composition is suitable in particular for the treatment of psoriasis. Consequently, another aspect of the present invention is the use of such a composition for the manufacture of a cream intended for the treatment of psoriasis.

Having now generally described the invention, a further understanding can be obtained by reference to certain specific Examples which are provided herein for purpose of illustration only and are not intended to be limiting unless otherwise specified. The amounts given in the following Examples are given in percent by weight.

EXAMPLES

| Example 1: Face cream | |
|---|---|
| A. Oily phase | |
| Dimethicone copolyol of formula (I) in pentacyclomethicone and water (10/88/2) (DC 5225 C) | 17.5% |
| B. Aqueous phase | |
| Sodium chloride | 2.5% |
| Glycerol | 5% |
| Preservatives | 0.55% |
| Citric acid | 0.035% |
| Water | 74.415% |

Procedure: Phase B is prepared by heating the mixture of sodium chloride, of glycerol and of preservatives in water to 45° C. with stirring until the preservatives have completely dissolved. The mixture is allowed to cool to room temperature and then citric acid dissolved in water is added thereto. Phase A is prepared by mixing the constituents with stirring and the mixture obtained previously is poured into phase A with stirring.

A white cream is obtained which has a viscosity, measured with a Rheomat 180, of 9.94 Pa.s (99.4 poises) at time zero. This viscosity stabilizes after 10 minutes at 7.01 Pa.s (70.1 poises).

| Example 2: body cream | |
|---|---|
| A. Oily phase | |
| Dimethicone copolyol of formula (I) in tetracyclomethicone and water (10/88/2) (DC 3225 C) | 6.25% |
| Tetracyclomethicone | 6.25% |
| B. Aqueous phase | |
| Sodium chloride | 2.5% |
| Polyethylene glycol 8 | 2% |
| Water | 83% |

Procedure: the various phases are prepared and phase B is introduced into phase A with stirring.

A white cream is obtained which has a viscosity, measured with a Rheomat 180, of 4.45 Pa.s (44.5 poises) at time zero. This viscosity stabilizes after 10 minutes at 3.88 Pa.s (38.8 poises).

The disclosure of French priority Application Number 9808418 filed Jul. 1, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A cosmetic or dermatological composition in the form of a cream, comprising: an aqueous phase dispersed in an oily phase with a silicone emulsifying agent, wherein the viscosity of the composition, measured with a Rheomat 180 viscometer at a shear rate of 200 s$^{-1}$ and at 25° C., ranges from 3 Pa.s (30 poises) to 20 Pa.s (200 poises), said aqueous phase constituting at least 78% by weight with respect to the total weight of the composition with the water of the aqueous phase constituting at least 65% of the total weight of the composition, and said emulsifying agent consisting of the dimethicone copolyol of formula (I):

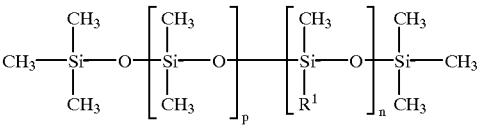

wherein R$^1$ is

p=394 and n=4.

2. The composition according to claim 1, wherein the emulsifying agent is mixed with at least one silicone oil.

3. The composition according to claim 1, wherein the emulsifying agent is present in an amount ranging from 0.5–5% by weight with respect to the total weight of the composition.

4. The composition according to claim 1, wherein the oily phase is present in an amount ranging from 8–22% by weight with respect to the total weight of the composition.

5. The composition according to claim 1, wherein the ratio by weight of oily phase to emulsifying agent is equal to or greater than 5.

6. The composition according to claim 1, which comprises at least one electrolyte.

7. The composition according to claim 6, wherein the electrolyte is present in an amount ranging from 0.5–20% of the total weight of the composition.

8. The composition according to claim 6, wherein the electrolyte is selected from the group consisting of salts of alkaline earth metal ions, alkali metal ion salts and potassium, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon and selenium salts, and their mixtures.

9. The composition according to claim 1, which comprises a physiologically acceptable medium and constitutes a topical composition.

10. The composition according to claim 1, which comprises at least one active ingredient selected from the group consisting of polyols, enzymes, natural extracts, procyanidol oligomers, vitamins, phosphate and glucosyl derivatives, urea, rutin, depigmenting agents, p-hydroxy acids, α-hydroxy acids, retinoic acid and its derivatives, screening agents, moisturizing agents and their mixtures.

11. The composition according to claim 1, wherein the aqueous phase constitutes at least 80 wt. % of the composition.

12. The composition according to claim 1, wherein water constitutes at least 70 wt. % of the composition.

13. The composition according to claim 1, which further comprises a mixture of Dead Sea salts.

14. A process for cosmetically treating the skin, hair, nails, scalp and/or mucous membranes, comprising:
   applying the composition of claim 1 to the skin, hair, nails, scalp and/or mucous membranes.

15. A method of treating greasy skin, comprising:
   applying the composition of claim 1 to greasy skin.

16. A method of treating psoriasis, comprising:
   applying the composition of claim 1 to the skin afflicted with psoriasis.

* * * * *

UNITED STATES PATENT AND TRADEMARK OFFICE
CERTIFICATE OF CORRECTION

PATENT NO. : 6,331,306 B1
DATED : December 18, 2001
INVENTOR(S) : Isabelle Afriat et al.

It is certified that error appears in the above-identified patent and that said Letters Patent is hereby corrected as shown below:

Column 6,
Line 12, replace "$(CH_3H_6O)-(C_2H_4O)_{18}-(C_3H_6O)_{18}H$" with -- $(C_3H_6O)-(C_2H_4O)_{18}-(C_3H_6O)_{18}H$ --

Signed and Sealed this

Fourth Day of June, 2002

Attest:

JAMES E. ROGAN
Attesting Officer
Director of the United States Patent and Trademark Office